United States Patent [19]

Brand

[11] Patent Number: 4,948,584

[45] Date of Patent: Aug. 14, 1990

[54] MODIFIED BEESWAX AND A PROCESS FOR THE MODIFICATION OF BEESWAX

[75] Inventor: Hans M. Brand, Nieuwerkerk, Netherlands

[73] Assignee: Koster Keunen Holland B.V., Bladel, Netherlands

[21] Appl. No.: 271,737

[22] Filed: Nov. 15, 1988

[30] Foreign Application Priority Data

Dec. 2, 1987 [NL] Netherlands ............... 8702899

[51] Int. Cl.$^5$ ............................................. A61K 6/00
[52] U.S. Cl. ....................................... 424/401; 424/70; 260/410.7
[58] Field of Search .................. 424/40, 20, 71; 514/786; 252/174.11; 260/410.7, 410.6; 106/270

[56] References Cited

U.S. PATENT DOCUMENTS

| | | | |
|---|---|---|---|
| Re. 29,649 | 5/1978 | Farnsworth | 252/174.11 |
| 2,612,509 | 9/1952 | Griffin | 260/410.6 |
| 3,821,372 | 6/1974 | Vanlerberghee et al. | 514/786 |
| 4,307,079 | 12/1981 | Zorayan et al. | 424/70 |
| 4,673,526 | 6/1987 | Zabotto et al. | 252/174.24 |

Primary Examiner—Ellis P. Robinson
Assistant Examiner—P. Prater
Attorney, Agent, or Firm—Webb, Burden, Ziesenheim & Webb

[57] ABSTRACT

The invention relates to a modified beeswax and to a process for this modification. The modification consists of a treatment of beeswax to remove free acids. According to the invention this can be accomplished by reacting the free acid present in beeswax with glycidol at a temperature of 80° C. to 120° C. in the presence of a basic catalyst. This modification results in an improvement of the properties of the beeswax. The modified beeswax being outstandingly suitable for use in cosmetic preparations whereby it does not cause any crystallization in the fatty phase. The modified beeswax has so called self-emulsifying characteristics and displays an outstanding dispersant action for solid substances. The compatibility with pigmented products and mixtures of mineral products in an oil phase is good.

10 Claims, 2 Drawing Sheets

Fig. 1

MODIFIED BEESWAX AND A PROCESS FOR THE MODIFICATION OF BEESWAX

The invention relates to modified beeswax and to a process for the modification of beeswax.

The modification of beeswax is generally known.

Beeswax is frequently used as a regulator for the consistency of cosmetic products. The emulsifying power of beeswax is also used in a basic medium; this can be achieved by reacting the free wax acids with base (borax), a "cold cream" being obtained (DE-A No. 3,407,821).

It was also already known to prepare self-emulsifying beeswax. A preparation of this type is effected by polyoxyethylation of the free beeswax acids.

From the Japanese Kokai Tokyo Koho JP No. 58, 92,605 in the name of Noda Wax K. K. it is known to esterify the free wax acids present in beeswax with cetyl, stearyl, oleyl or isostearyl alcohol and glycerol. By this means a product is obtained which is considerably softer than the untreated product. The esterification is carried out at 80° to 120° C. for 10 to 16 hours using sulphuric acid as the catalyst. After the reaction has stopped, the sulphuric acid is neutralized with base.

The characteristics of the product obtained are, however, not yet satisfactory. Specifically, the use of strong inorganic acids, such as sulphuric acid, phosphoric acid or hydrochloric acid, or strong organic acids, such as p-toluenesulphonic acid or methanesulphonic acid, leads to oxidation, as a result of which a strong colouration of the wax arises. As a consequence, the wax has to be bleached or decolourized after the esterification is complete in order to make it suitable for use in cosmetic preparations.

For incorporation in the fatty phase of a cosmetic (or other) product it is desirable that no crystallization occurs, even after standing for a prolonged period. The occurrence of crystallization is, however, a disadvantage which frequently arises even with good quality bleached beeswax. Crystallization can cause phase separation in the cosmetic emulsion, as a result of which the product becomes less usable but also suffers in appearance. The appearance is, of course, of great importance in cosmetic products.

In order to prevent crystallization in the fatty phase, an attempt can be made to avoid this as much as possible by incorporating components which combat, or at least do not promote, crystallization in the cosmetic preparations.

A number of other consistency-imparting substances, i.e. stabilizers for the fatty phase, than beeswax are also known. These are based on a different principle and impart stability to a dispersion; these are, for example, bentonites, hectorites, silicas and aluminas. Products of this type are not soluble in the fatty phase.

It has now been found that by the modification of beeswax a product can be obtained which is outstandingly suitable for use in cosmetic preparations and then does not cause any crystallization in the fatty phase. This modified beeswax is characterized in that it contains no or virtually no free acids. A modified beeswax which does not cause crystallization is novel. It was not to be expected that a treatment which results in there being no or virtually no further free fatty acids present would give this result. The modified beeswax according to the invention has so-called self-emulsifying characteristics. This means that under favourable circumstances no co-emulsifier is needed. The modified beeswax also displays an outstanding dispersant action for solid substances. Solid substances of this type (such as, for example, kaolin) are frequently processed in cosmetics. The compatibility with pigmented products and mixtures of mineral products in an oil phase is good.

Figure 1:
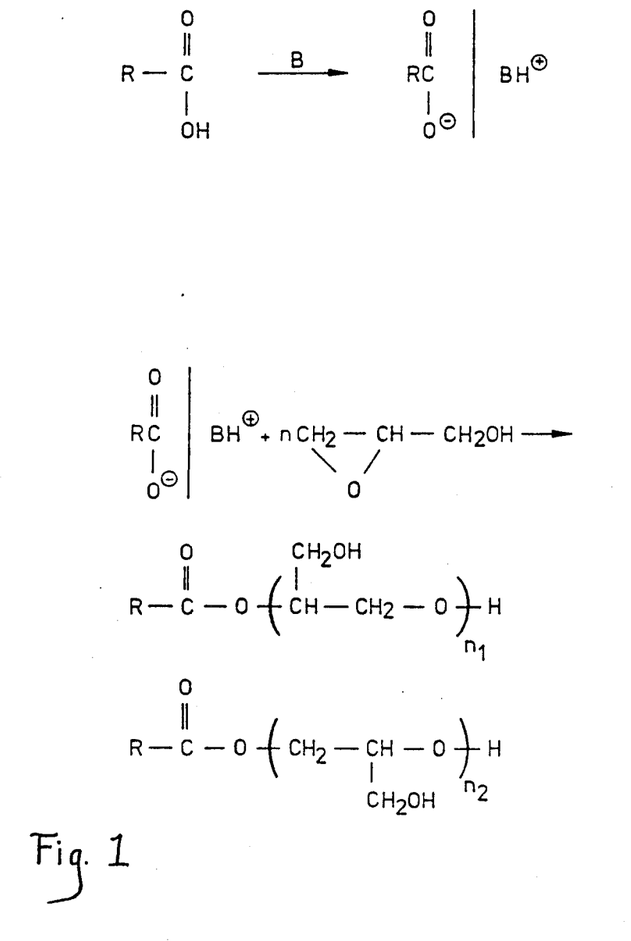

The free acids can appropriately be removed from the beeswax with the aid of glycidol (2,3-epoxy-1-propanol) under the influence of basic catalysts and a reaction at a temperature of 80° to 150° C. (see FIG. 1). Appropriately 0.0005–3% by weight, preferably 0.05–0.5% by weight and in particular 0.1% by weight of base, relative to the free acids in beeswax, is used for this purpose. The modification is effected by bringing the beeswax into contact at the reaction temperature of 80° to 150° C. with the base used as the catalyst and then adding the glycidol dropwise. Within this range, the temperature does not influence the quality of the end product. The use of glycidol has, inter alia, the following advantages over the use of ethylene oxide.

(a) The reaction can be much better controlled.

(b) The boiling point of ethylene oxide is 11° C., with the consequence that handling is more difficult than with glycidol, which has a favourable boiling point.

(c) With ethylene oxide the reaction is particularly exothermic, as a result of which the reaction is a-selective.

A particularly suitable basic catalyst is potassium carbonate; other basic catalysts which can be used are potassium hydroxide, mono-, di- and tri-ethanolamine and sodium alcoholates. When potassium hydroxide is used as the catalyst, 0.05 to 1.0% by weight is employed. In this case addition to the free hydroxyl groups also takes place. The self-emulsifying character of the modified beeswax is then stronger.

If ethanolamines are used as the catalyst (in an amount of 5 to 20% by weight), addition of glycidol to the ethanolamine also takes place. The presence of addition products of the ethanolamine and glycidol gives rise to a higher hydrophilicity of the end product. These products act as an emulsifier and are soluble both in the beeswax phase and in water.

For the reaction with the acids, a minimum amount of 2.4 mol of glycidol per mol of beeswax is required. With a lower molar ratio the product has a residual acid number and is not amorphous. If more than 4 mol of glycidol per mol of beeswax acids are used, no additional advantage results from the addition of extra glycidol.

The formation of polyglycerol is to a great extent determined by the rate at which the addition takes place. The mechanism of the formation of polyglycerol is known from E. J. Vanderberg J. Pol. Sci., 23, 915–945 (1985). A metering rate of 23 mmol per minute/kg wax resulted in a small amount of polyglycerol and nevertheless makes a relatively easy preparation possible. When working with large amounts, a favourable rate of addition is 15–40 mmol glycidol per kg beeswax per hour.

The reaction is strongly exothermic and it is therefore advisable not to choose the starting temperature of the reaction too high. On average, a temperature rise of approximately 30° C. must be expected.

During the reaction polyglycerol is formed, depending on the concentration and the nature of the catalyst, the reaction temperature and the manner of addition of the glycidol (rate, solvent). The polyglycerol formed is insoluble in the acid-free beeswax thus obtained. A two-phase system is formed. The polyglycerol forms the bottom layer in this system. The two phases can be separated from one another by decanting and the modified beeswax is washed with water to which a little dilute mineral acid (for example phosphoric acid, which is not soluble in the modified beeswax) has been added. Other mineral acids, such as, for example, hydrochloric acid, can also be used. The sole requirement is that the acid does not have any oxidizing properties and is not soluble in the wax.

Preferably, the product obtained is washed with 0.1N orthophosphoric acid, while sulphuric acid can also be used. The reason for washing in an acid medium is the removal of residual basic catalyst and to allow phase separation to take place more easily.

If a suitable demulsifier is used, the washing process can take place without intermediate separation of the polyglycerol formed.

With the process according to the invention, it is not necessary to use demineralized water since the contaminants (Ca, Mg, Al and the like) show no interaction with the end product (it was then also not possible to detect any difference between the product washed with demineralized water and that washed with non-demineralized water).

The small amounts of polyglycerol which are still present are removed during the washing process by extraction. Any polyglycerol which may be present has a fairly severe influence on the characteristics of the modified beeswax and therefore the washing process influences the characteristics of the product obtained to a high degree.

It was found that heating the modified beeswax to 150° C. has no influence on the characteristics. Moreover, no oxidation takes place at this temperature. Heating the product to 250° C. for 2 hours did not adversely affect the colour.

During the reaction the free wax acids, as these occur in beeswax, are, as mentioned above, converted to the corresponding polyglycerol esters. The degree to which this takes place determines (wholly or in part) the characteristics of the modified beeswax. In a series of tests various gradations of modified beeswax have been made in which the length of the polyglycerol chain was varied and in which (limited) amounts of free wax acids were still present.

During cooling, the modified beeswax obtained exhibits a contraction which can amount to 30 to 35%, depending on the cooling gradient. A severe contraction of this type is typical of amorphous materials.

The modified beeswax is capable of gelling fluid oils and other waxes (paraffin oil, sesame oil, peanut oil, avocado oil, almond oil, jojoba oil, oleyl oleate, decyl oleate, isopropyl myristate, isopropyl palmitate, PCL liquid (which is a mixture of esters with long branched chains, Dragoco), synthetic triglycerides such as Myglycol 812 (Dynamit Nobel), liophilic silicone oils, etc.), the viscosity of the oil being co-determining for the amount of beeswax to be used. Mixtures of lipophilic components can also be converted to a stable, non-crystalline gel in this way.

The modified beeswaxes according to the invention are suitable for the preparation of so-called micro- and nano-capsules, which are frequently used in high quality cosmetics and for which the use in pharmaceuticals is now being developed.

When the hydrophilicity of the component to be gelled is too great (such as, for example, in the case of lower alcohols, such as ethanol and isopropanol), no gel formation takes place. The presence of a small amount (preferably not more than 10% by weight based on the total amount) of higher saturated alcohols, that is to say having at least 12 carbon atoms (lauryl alcohol), but especially 16 to 18 carbon atoms is possible without this resulting in the gel structure being lost and crystallization occurring. Higher unsaturated alcohols (having at least 12 carbon atoms) do not interfere.

The quality of the gel obtained was assessed on various properties, specifically:
 (a) the degree of crystallization;
 (b) de-mixing as a function of time;
 (c) viscosity and (possibly) flow characteristics;
 (d) lubricating characteristics.

The sum of these effects was indexed between 0 and 10 (subjective observation) and compared with a reference preparation with 100% beeswax in the same composition.

For all hydrophobic oils, waxes and fats investigated it was possible to prepare a stable gel which was assessed with a rating of 7 to 8. The assessment of the corresponding composition with 100% beeswax (not modified) was usually no higher than 2 to 2.5 and the maximum value was 3.5.

In certain cases these gels can be used directly as a cosmetic preparation, specifically in vegetable extracts in mineral oil and products of this type; the quality of the gel also initiates the use of the modified beeswax in emulsions and "stick" formulations. A controllable consistency of the oil phase, without crystallization occurring, is desirable for all cosmetic emulsions and determines the degrees of freedom for the composition of the formulation. The use of the modified beeswax according to the invention gives a greatly increased stability of the fat phase and a stability of this type can be measured on the basis of the gel formation.

The colour of the beeswax (Apis mellifera) to be used as the starting material is not important, that is to say it is possible to start from bleached or unbleached beeswax, irrespective of the origin.

In the reaction used for rendering acid-free, the free hydroxyl groups can also react with the glycidol when the free acid content falls. Thus, in fact, a side reaction occurs. This side reaction can have the consequence that a product with a small amount of free acid does not always have a better action than a product with a somewhat greater amount of free acid.

GMBW-2, defined below is particularly suitable for gelling hydrophobic products in the presence of dermatologically active products or of products which can be metabolized by the skin.

All tests in the present application were carried out with beeswax of Apis mellifera.

The modified beeswax according to the invention is particularly suitable for gelling hydrophobic products in the presence of dermatologically active products, specifically if these products are insoluble in water or are susceptible to hydrolysis. Examples of products of this type are plant extracts, solutions of vitamins (including vitamin A, D2, E, K etc.), provitamins (for example carotene, lycopene and bixins) and dermatologically active compounds.

It was found that in low concentrations (for example 0.1% by weight) these products do not have an adverse effect on the gel formation of the oils described with modified beeswax. Thus, stable gels which do not have a granular character (that is to say exhibit no crystallization phenomena) are obtained from 80% paraffin oil and 20% modified beeswax in the presence of carotene (0.1% by weight) and bixin (0.1% by weight; E160, dimethylnorbixin or bixin). The hydrophobic extract of Aloë Vera (Aloë vera lipoquinone ®/Terry Corp.) can also be gelled. These gels are suitable for direct application to the skin. The corresponding product in which modified beeswax is replaced by normal beeswax does not have this characteristic.

EXAMPLE I

The modification of beeswax with glycidol.

1320 g white beeswax were melted and brought to 90° C. in a four-necked flask with a capacity of 2 l, provided with a stirrer, a dropping funnel, a thermometer and a sample gate. 65 mg anhydrous potassium carbonate was then added and the mixture was stirred until all solid matter had dissolved. 127 ml (139.3 g/1.88 mol) 2,3-epoxy-1-propanol (glycidol) was then added to the reaction mixture at a rate of 2 ml/min. During the addition the temperature of the reaction mixture rose to 120° C. After the addition was complete, the mixture was stirred for a further one hour; during this period some polyglycerol was formed which is insoluble in the modified beeswax. The reaction mixture was then given the opportunity to separate into two phases. The modified beeswax constituted the top layer and the polyglycerol the bottom layer.

After separating the two phases, the modified beeswax was washed with 450 ml demineralized water and 50 ml 0.1N phosphoric acid. After phase separation, the product was washed once more with water to remove residues of mineral acid. The modified beeswax obtained in this way was rendered anhydrous by heating to 135° C. and filtered. The product has an acid number lower then 0.1 (that is to say it cannot be determined when the customary analytical procedure for the determination of the acid number of waxes, as is described in various pharmacopoeia, is used).

The identification numbers of the original beeswax can be used to calculate the identification numbers of the modified beeswax.

Calculated on the basis of the specifications (Ph.Eur. acid number is 17–22; ester number is 70–80), an increase in weight of 26.5 g per mol glycidol is obtained per kg beeswax; the ester number of the modified beeswax can be calculated using the equation:

ester number = 1000 × saponification number/(1000+n×26.5), in which n is the mean chain length of the polyglycerol. The saponification number is defined as the sum of the acid number and ester number. This equation can be represented as:

E.V. = 1000 × SAP/(1000+n×26.5).

The iodine number decreases as a result of the relative increase in weight. The specification for the iodine number of beeswax is about 8–12 and decreases to 7–11. No statement can be made with regard to the acetyl number (hydroxyl number) because the hydroxyl number can decrease as a result of the addition of glycidol to the free hydroxyl groups. The degree to which this takes place is dependent on the base strength of the catalyst used and the absolute amount thereof.

The product obtained no longer has a definite solidification point but a range within which the material solidifies. According to the observations, the solidification range is between 72° and 66° C. depending on the degree of addition (per product the solidification range extends over about 3° C.). The melting point is also not definite; there is clear evidence of a melting range, which is dependent on the degree of addition.

EXAMPLES II–XIX

Various gradations of modified beeswax in which the calculated chain length of the polyglycerol fatty acid esters was set to 2.4; 4.8; 7.2; 9.6 and 12.0 were prepared; these were designated modified beeswax (GMBW-1 to GMBW-5). A number of characteristics are indicated in the table below, in which the starting material (BW) is also included.

|        | Acid number | Ester number | Saponification number | Solidification point °C. |
|--------|-------------|--------------|------------------------|--------------------------|
| BW     | 19.2        | 75.1         | 94.3                   | 61.5 C.                  |
| GMBW-1 | 4.2         | 85.4         | 89.6                   | 71.5 C.                  |
| GMBW-2 | <0.1        | 89.9         | 89.9                   | 66.5 C.                  |
| GMBW-3 | <0.1        | 89.7         | 89.7                   | 64.5 C.                  |
| GMBW-4 | <0.1        | 90.3         | 90.3                   | 66.0 C.                  |
| GMBW-5 | <0.1        | 92.3         | 92.3                   | 64.5 C.                  |

In the case of GMBW-1 virtually no polyglycerol was formed and it was found from a separate test that the product obtained has emulsifying properties. Phase separation could be achieved only by adding a demulsifier to a mixture of GMBW-1 and water (40:60).

Tests with single oils and waxes (Examples II–X)

Peanut oil, avocado oil, sesame oil, castor oil, Myglyol 812, jojoba oil, isopropyl myristate, isopropyl palmitate and PCL liquid were tested. The quality of the gel obtained was assessed with a value of 0 (absolutely unusable) to 10 (perfect). The requirement for a perfect gel was that the product obtained exhibits no flow phenomena, no granular structure and phase separation and has a low penetration. In general, it can be stated that the quality with an assessment of 4 to 5 can still be regarded as adequate.

EXAMPLE II

Peanut oil

Concentration used 11% GMBW-x+89% peanut oil.

With BW (untreated beeswax) a highly granular mass was obtained from which oil separated. The product obtained had a low viscosity (qual=1.0; qual - quality on a scale from 1 to 10 where 1 is the lowest and 10 the highest).

With GMBW-1 a moderately granular semi-fluid was obtained from which no separation of oil was detected (qual=1.5–2.0). These two gels were characterized as inadequate.

Samples GMBW-2 to GMBW-5 inclusive exhibit no granular characteristics, no flow characteristics and no demixing phenomena. They can be characterized as virtually perfect gels. The quality of the various gels was determined as 9 (GMBW-2) to 8 (GMBW-5). The intermediate modified beeswaxes have a value in between. It is pointed out here that it is hardly possible to differentiate between these various qualities.

EXAMPLE III

Avocado oil

Concentration used: 11% GMBW-x + 89% avocado oil

The results which were obtained with this oil were equivalent to the results obtained with peanut oil. In this case also a sample with BW was very poor (highly granular, fluid, phase separation; qual=1.0) and a sample with GMBW-1 was too fluid (qual=1.5–2.0). Both samples were of inadequate quality. Here also it can be stated that GMBW-2 to GMBW-5 inclusive gave an equivalent result, with a slight preference for GMBW-2 (qual=9.0–7.0).

EXAMPLE IV

Sesame oil

Here also the same concentrations were used as in the case of avocado oil. Similar results were obtained.

| | |
|---|---|
| BW | qual = 1.0 |
| GMBW-1 | qual = 2.0 |
| GMBW-2 | qual = 9.0 |
| GMBW-3 | qual = 8.5 |
| GMBW-4 | qual = 8.0 |
| GMBW-5 | qual = 7.0 |

EXAMPLE V

Castor oil

In this example the concentration BW/GMBW-x (x=1–5) was the same as in the previous examples. The results obtained were similar. The sample with GMBW-2 was assessed as being of quality 10. The quality of the gel is particularly good.

EXAMPLE VI

Myglyol 812 ® (a triglyceride of fatty acids having 8–12 carbon atoms).

This product is used extensively in practice in cosmetic formulations. It was found that this product was inadequately gelled by BW and GMBW-1 and the product obtained is not very suitable for use. The GMBW-2 to GMBW-5 products, however, did meet the minimum requirements as are laid down by the quality of the gel.

| | |
|---|---|
| GMBW-2 | qual = 5.0 |
| GMBW-3 | qual = 4.0 |
| GMBW-4 | qual = 4.0 |
| GMBW-5 | qual = 4.5 |

A slight degree of phase separation, which could be nullified by homogenization, was observed in the case of GMBW-4 and GMBW-5. As a consequence of the viscosity of Myglyol 812, however, the same good result as in the case of four preceding glyceridic oils was not obtained. This is incidently a general principle; the lower the viscosity of the medium to be gelled the more difficult it is to effect gelling.

Nevertheless an improvement is discerned when GMBW-2 to GMBW-5 are used in higher concentration.

With regard to the gels of the peanut oil, sesame oil and castor oil it is pointed out that cooling the gel to −8° C. has no consequences for the quality and stability of the gel. In the case of Myglyol 812, when 11% GMBW-2 to GMBW-5 is used, an increased degree of phase separation is, however, observed.

EXAMPLE VII

Jojoba oil

A concentration of 11% by weight GMBW-x + 89% by weight jojoba oil was used.

With BW a granular mass was obtained (qual=2.5), which, however, did have a reasonable consistency. With GMBW-1 a fluid product was obtained which had slightly granular characteristics. GMBW-2 to GMBW-5 inclusive show a very great deal of correspondence with one another, although GMBW-4 and GMBW-5 appeared to be somewhat better. In this context it is mentioned that repeated heating to 130° C. and cooling to room temperature levelled out the differences between the various samples (of course, heating jojoba oil to 130° C. is not desirable).

EXAMPLE VIII

Isopropyl myristate

Concentration used: 20% by weight GMBW-x + 80% by weight isopropyl myristate.

As a consequence of the great difference in viscosity between the starting materials it is necessary to stir slightly during cooling in order to prevent a temperature gradient as far as possible.

| | |
|---|---|
| BW | qual = 1.0 |
| GMBW-1 | qual = 2.5 |
| GMBW-2 | qual = 4.0 |
| GMBW-3 | qual = 5.0 |
| GMBW-4 | qual = 6.0 |
| GMBW-5 | qual = 6.0 |

EXAMPLE IX

Isopropyl palmitate

| | |
|---|---|
| BW | qual = 1.0 |
| GMBW-1 | qual = 2.5 |
| GMBW-2 | qual = 4.0 |
| GMBW-3 | qual = 5.0 |
| GMBW-4 | qual = 6.0 |
| GMBW-5 | qual = 6.0 |

EXAMPLE X

PCL liquid ® (Dragoco)

Concentron used: 20% by weight GMBW-x + 80% by weight PCL liquid.

Only BW and GMBW-2 were tested for this product. The product with BW was granular, showed phase separation and had a low viscosity (qual=2.0); the product with GMBW-2, on the other hand, was an attractive smooth gel which was not granular. This product must definitely be characterized as one of the better products. As a consequence of the high concentration of GMBW-2, the viscosity of the gel obtained was (unexpectedly) high. This is remarkable because the viscosity of PCL liquid is low. Stirring during cooling was not necessary.

EXAMPLE

Investigation into the use of a mixture of modified beeswax and white beeswax.

For this series of tests use was made of GMBW-2 as the modified beeswax and mixtures of GMBW-2 with white beeswax for gelling of peanut oil.

| % GMBW-2 | % white beeswax | Remarks |
|---|---|---|
| 100 | 0 | qual = 10.0 |
| 80 | 20 | qual = 8.0 |
| 60 | 40 | qual = 7.0 |
| 40 | 60 | qual = 4.5 |
| 20 | 80 | qual = 4.0 |
| 0 | 100 | qual = 1.0 |

Despite the fact that peanut oil can be gelled relatively easily, the use of small contents of white beeswax leads to an inadequate quality of the gel. For other oils and fluid waxes a considerably stronger influence on the quality of the gel obtained is observed in all cases.

EXAMPLE XI

For the use of GMBW-2 for gelling silicone oils, the following silicone oils were investigated.

| Dow Corning 556 fluid | (DC 556) |
|---|---|
| Dow Corning 593 fluid | (DC 593) |

The gel formation of DC 556 and DC 593 was tested with 10.15 and 20% of GMBW-2 and BW respectively; in all cases a highly granular product with which phase separation occurred was obtained with BW. In these cases there was then no question of gel formation.

In the following table a similar quality standardization is used to that in the experiments with vegetable and (semi)-synthetic oils.

TABLE A

|  |  | 10% GMBW-2 | 15% GMBW-2 | 20% GMBW-2 |
|---|---|---|---|---|
| (a) | DC 556 | 7 | 9 | 10 |
| (b) | DC 593 | 5 | 6 | 8 |

Gelling was not readily possible when other silicone oils (polydimethylsiloxane); cyclic tetramers and pentamers (dimethylsiloxane) were used. It was possible to gel other siloxanes substituted by phenyl groups, which are comparable with DC 556 and DC 593.

EXAMPLE XII

Use of GMBW-2 with mixtures of various oils and fluid waxes and isopropyl esters.
GMBW-x (11%)+IPP (30%)+peanut oil (41.3%)+jojoba oil (41.3%)

| BW | qual = 3.0 | (granular but stable) |
|---|---|---|
| GMBW-1 | qual = 4.5 | (granular, fluid) |
| GMBW-2 | qual = 6.5 | (not granular) |
| GMBW-4 | qual = 5.5 | (not granular but poorer than with GMBW-2) |

GMBW-2 was found to perform well in this mixture; the gel showed no crystallization even at low temperature (4° C.).

EXAMPLE XIII

GMBW-x (11%)+IPP (30%)+peanut oil (17.7%)+jojoba oil (41.3%)

| BW | qual = 3.0 | (as in XII) |
|---|---|---|
| GMBW-1 | qual = 5.5 | (better than in XII) |
| GMBW-2 | qual = 8.0 | (very good gel) |
| GMBW-4 | qual = 7.0 | (very good gel) |

GMBW-2 was found to perform well in this mixture; the gel showed no crystallization even at low temperature (4° C.).

EXAMPLE XIV

BW/GMBW-x (11%)+jojoba oil (44.5%)+almond oil (44.5%)

| BW | qual = 3.5 | (granular, high viscosity) |
|---|---|---|
| GMBW-2 | qual = 8.0 | (very good gel) |

EXAMPLE XV

BW/GMBW-X (11%)+jojoba oil (44.5%)+avocado oil (44.5%)

| BW | qual = 3.5 | (as in XIV) |
|---|---|---|
| GMBW-2 | qual = 7.0 | (good gel) |

EXAMPLE XVI

BW/GMBW-x (11%)+Myglyol 812 (44.5%)+oleyl oleate (44.5%)

| BW | qual = 2.0 | (very poor product) |
|---|---|---|
| GMBW-2 | qual = 6.5 | (good gel also in view of the low viscosity of the starting materials) |

EXAMPLE XVII

Multicomposition

The following were used for this: A % by weight BW/GMBW-x and B % by weight of, respectively, jojoba oil, avocado oil, Myglyol 812, oleyl oleate, isopropyl myristate and paraffin oil. A=10; B=15

| BW | qual = 2.0 | (very poor product) |
|---|---|---|
| GMBW-2 | qual = 8.0 | (very good) |

EXAMPLE XVIII

As Example XVII but A=13; B=14.5

| BW | qual = 2.0 | (very poor product) |
|---|---|---|
| GMBW-2 | qual = 6.5 | (good gel but too much GMBW-2) |

EXAMPLE XIX

As Example XVII but A=16; B=14

| BW | qual = 1.0 | (very poor product) |
|---|---|---|
| GMBW-2 | qual = 4.0 | (slightly granular character; GMBW- |

-continued 2 concentration too high)

The tests as described in Examples XVII–XIX indicate to what extent and in what concentration GMBW-2 can be used for gelling the fatty phase.

EXAMPLE XX

In Table B a number of tests are shown for the determination of the influence of the presence of polyglycerol on the appearance of gels GMBW-2 fatty phases and the determination of the optimum concentration of GMBW-2 for use. The following were used for these tests:
1. White beeswax (BW)
2. GMBW-2 in which polyglycerol is present (less than 0.1% by weight)
3. GMBW-2 free from polyglycerol.

The results obtained are shown in Table B.

It can be seen that in the presence of polyglycerol esters with straight chains can be better gelled by GMBW-2 than glyceridic oils, and vice versa. In the absence of polyglycerol the glyceridic esters can be better gelled by GMBW-2 than esters with straight chains. For paraffin oil there appears to be a slight preference for the presence of low percentages of polyglycerol.

With regard to the optimum concentration for use, it can be stated that, as an average value, this is about 9%, although this is dependent on the oil to be gelled.

| Oil phase | | 5% by weight | 9% by weight | 12% by weight | 15% by weight | 18% by weight |
|---|---|---|---|---|---|---|
| Jojoba oil | 1 | 1* | 1* | — | 2 | — |
| | 2 | 5 | 7 | — | 4 | — |
| | 3 | 2* | 4 | — | 3 | — |
| Decyl oleate | 1 | 1 | 1* | — | 2 | — |
| | 3 | 4 | 9 | — | 7 | — |
| Oleyl oleate | 1 | 2* | 1 | — | 1 | — |
| | 2 | 4 | 9 | — | 7 | — |
| | 3 | 3 | 6 | — | 4 | — |
| Paraffin oil | 1 | 2–3 | 2 | — | 1 | — |
| | 2 | 7 | 8 | — | 8 | — |
| | 3 | 3 | 4 | — | 6 | — |
| Peanut oil | 1 | 2 | 1 | 1 | 1 | 1 |
| | 2 | 8 | 5–6 | 4 | 2–3 | 2 |
| | 3 | 6 | 10 | 8–9 | 8–9 | 7 |
| Avacado oil | 1 | 2 | 1 | — | 1 | — |
| | 2 | 9 | 6 | — | 3 | — |
| | 3 | 9 | 9 | — | 7 | — |
| Sesame oil | 1 | — | 2–3 | — | — | — |
| | 2 | — | 4 | — | — | — |
| | 3 | — | 9 | — | — | — |
| Castor oil | 1 | — | 1 | — | — | — |
| | 2 | — | 3 | — | — | — |
| | 3 | — | 8 | — | — | — |
| Oleyl alcohol | 1 | — | 1–2 | — | — | — |
| | 3 | — | 7 | — | — | — |
| Myglyol 812 | 1 | 2 | 1* | — | 1 | — |
| | 3 | 4–5 | 8 | — | 6–7 | — |

*phase separation

Applications of GMBW-2 in cosmetic emulsions

GMBW-2 can be used in oil-in-water (O/W) and water-in-oil (W/O) emulsions.

EXAMPLE XXI

Emulsions can be prepared in the following way. Firstly an oil-containing phase and a water-containing phase are prepared. The two phases are then warmed to 70° C.; the organic phase is added to the aqueous phase and the mixture emulsified with stirring (3000 revolutions per minute). Stirring with a paddle stirrer (20 revolutions per minute) is continued during cooling, and after cooling to 35° C. the emulsion obtained is transferred to a suitable container.

The phases can, for example, have the following composition.

| Phase A | |
|---|---|
| Beeswax or modified beeswax (GMBW-2) | 11 g |
| Paraffin oil | 40 g |
| Span 40 | 3 g |
| Phase B | |
| Tween 40 | 2 g |
| Preservative | 0.5 g |
| Water | 43.5 g |

Difference between the two emulsions:
1. The emulsion with modified beeswax was butter-like and had a heavy consistency while the emulsion with normal beeswax had a watery feel and a considerably lighter consistency.
2. The emulsion with modified beeswax gives an improved feeling to the skin (felt "warm"), while the emulsion with normal beeswax felt "cold" and unpleasant.
3. The emulsion with modified beeswax had a particularly "full" appearance.
4. The emulsion with modified beeswax drew no threads, did not "soap" and spread perfectly on the skin; the emulsion with normal beeswax showed a thready character and soaped on the skin. The rubbing characteristics of the two emulsions were in other respects identical.
5. The emulsion with normal beeswax was whiter than that with modified beeswax.
6. The emulsion with the modified beeswax was somewhat matter than the emulsion with normal beeswax.

EXAMPLE XXII

The following components were subjected to the procedure described in Example XXI:

| Phase A | |
|---|---|
| Beeswax/GMBW-2 | 4 g |
| Cetyl alcohol | 1 g |
| Stearic acid | 1 g |
| Paraffin oil | 5 g |
| Lanolin | 2 g |
| Castor oil | 1 g |
| Arlacel 60 | 2 g |
| Phase B | |
| Glycerol | 3 g |
| Triethanolamine | 1 g |
| Tween 60 | 1 g |
| Preservative | 0.5 g |
| Water | 78.5 g |

Points of difference between the two emulsions:

Apart from a considerably improved feeling on the skin as a result of the use of modified beeswax, there are not many great differences between the two emulsions to be indicated. In the case of the modified beeswax it can be mentioned that the emulsion is somewhat less troubled by occlusion of air and that the emulsion is somewhat more stable. Over a period of one hour at 110° C. this emulsion still did not show any phase separation, but the emulsion with normal beeswax did.

It can be seen from this example that the presence of stearic acid must be considered undesirable. To what extent unsaturated fatty acids also influence the quality of the emulsion cannot be derived from this experiment.

EXAMPLE XXIII

The procedure described in Example XXI was followed and the following components were used.

| Phase A | |
|---|---|
| Peanut oil | 20 g |
| Beeswax/GMBW-2 | 3 g |
| Cetyl alcohol | 1 g |
| Arlacel 60 | 2 g |
| Phase B | |
| Tween 60 | 3 g |
| Preservative | 0.5 g |
| Water | 69.5 g |

Differences between the two emulsions.

1. The emulsion with modified beeswax has an appreciably heavier consistency than the emulsion with normal beeswax.
2. The emulsion with modified beeswax feels stiffer and butter-like, while the emulsion with normal beeswax has a "flaccid" consistency and feels watery.
3. The rubbing characteristics of the emulsion with normal beeswax are good, but the rubbing characteristics of the emulsion with the modified beeswax are considerably better. Use of modified beeswax gives a greatly improved feeling on the skin.
4. The emulsion with modified beeswax does not soap; that with normal beeswax soaps somewhat.
5. The emulsion with modified beeswax is more stable than the emulsion with normal beeswax.

The unsaturated fatty acids which are present in the peanut oil do not interfere. This is in contrast to saturated fatty acids such as stearic acid and palmitic acid. The free unsaturated acids also did not interfere in emulsions in which sesame oil, avocado oil and wheatgerm oil were processed.

EXAMPLES XXV, XXVI and XXVII

EXAMPLE XXIV

Use of GMBW-2 in pigmented products and mixtures of mineral products and an oil phase.

With the aid of modified beeswax (GMBW-2) it is possible to make very stable dispersions of products 1 to 13 below which can be used for application in flowable powders, face masks, lipsticks, pigmented creams, flowable bulk powders, foundation creams, coloured pastes, mascaras and peel-off products.

| | Pigments tested (organic) | |
|---|---|---|
| 1. C.I. 15585:1 | Pigment Red 53:1 | D&C Red 9; Ba-lake |
| 2. C.I. 15985:1 | Pigment Yellow 104 | D&C Yellow 6; Al-l 6; Al-lake |
| 3. C.I. 19140:1 | Pigment Yellow 100 | FD&C Yellow 5; Al-lake |
| 4. C.I. 42090:2 | Acid Blue 9 | FD&C Blue 1; Al-lake |
| 5. C.I. 45170:3 | Pigment Red 173 | D&C Red 19; Al-lake |
| | Pigments tested (inorganic) | |
| 6. C.I. 77163 | Pigment White 14 | Bismuth oxychloride |
| 7. C.I. 77491 | Pigment Red 101 | Iron oxide |
| 8. C.I. 77492 | Pigment Yellow 42 | Iron oxide |
| 9. C.I. 77742 | Pigment violet 16 | Manganese violet |

Inorganic materials
10. Kaolin (aluminium silicate hydrate)
11. Aerosil (very finely divided $SiO_2$ obtained by burning a mixture of silanes).
12. Aluminium oxide (passed through a sieve with 0.104 mm openings)
13. Titanium dioxide (anatase; Merck No. 23.203-03)

The dispersions of products 1 to 13 were tested in the presence of: paraffin oil, castor oil, DC 556 and DC 593.

Three series of experiments were carried out, these being with a total loading of pigment or inorganic product of 5, 10 and 15% by weight.

The total sample size was always 25 g.

Each of the experiments described above was carried out at four concentrations GMBW-2: 5%, 10%, 15% and 25%, based on weight.

The pigments or inorganic products were melted together (T=75° C.) with GMBW-2 and mixed until the pigment or the inorganic product was dispersed as well as possible and no further (visible) aggregates were present. The oil was then added and the whole homogenized.

1. The organic coloured pigments (1–5)

Very stable dispersions were formed of the pigments in GMBW-2 when the weight ratio (pigment/GMBW-2) was not greater than 2. At higher weight ratios destabilization of the dispersion was observed (2 hours; 75° C.), the pigment separating out again.

Addition of paraffin oil, DC 556 and DC 593 no influence on the stability of the dispersion obtained (60° C.; 2 hours).

After cooling a gel was formed which showed no granular characteristics but the consistency of which was considerably higher than that of a comparable gel of GMBW-2 with the particular oil in the presence of the pigment.

When castor oil was used, a substantial increase in the consistency was observed as a result of the presence of the pigment. Mixtures of pigment, GMBW-2 and castor oil with a loading of pigment of 5 and 10% by weight GMBW-2 already no longer showed any flow characteristics and could no longer be applied easily to the skin. Identical mixtures of GMBW-2 and castor oil without pigment had a considerably less heavy consistency and could readily be applied to the skin. Apparently there is an interaction between the pigment and castor oil and it is not precluded that this arises by the formation of hydrogen bridges between the strongly polar pigment and the hydroxyl groups of the castor oil.

When beeswax is used in place of GMBW-2, a stable dispersion of the pigment is not formed, but a highly granular mass is formed. GMBW-2 is therefore an outstanding dispersant for organic coloured pigments, but the weight ratio of the pigment and GMBW-2 is subject to an upper limit.

2. The inorganic pigments

The experiments were carried out in an identical manner. For manganese violet (C.I. 77742; Pigment Violet 16) the same conclusion applies as for the five organic coloured pigments investigated.

For iron oxides, on the other hand, the (pigment/GMBW-2) ratio is clearly different. In this case the maximum ratio which can be used is 0.8–1; at higher ratios destabilization occurs. The gels obtained are also of a less fine appearance and show the tendency to crystallization more rapidly.

With ratios of less than 0.8 stable products are obtained.

Bismuth oxychloride (C.I. 77163; Pigment White 14) can be used in ratios of up to a maximum of 1.2–1.4; at higher ratios destabilization occurs.

3. Inorganic materials

Kaolin and Aerosil were easy to disperse with the aid of GMBW-2 without there being restrictions on the ratio of inorganic product/GMBW-2. In all cases the dispersions obtained were stable. Specifically in the case of the use of Aerosil, it was found that the consistency is highly dependent on the amount of inorganic material used. In the case of aluminium oxide and titanium dioxide (both 150 mesh) it was found that the weight ratio inorganic product/GMBW-2 is subject to an upper limit. For the given particle size this was 1.5; this ratio is a function of the mean particle size.

The stable dispersions obtained as described above can therefore be used to obtain particularly stable pigmented emulsions.

EXAMPLE XXV

Day cream

| Phase A | |
|---|---|
| Paraffin oil | 8% by weight |
| Peanut oil | 8% by weight |
| Avocado oil | 2% by weight |
| Wheatgerm oil | 2% by weight |
| GMBW-2 | 5% by weight |
| Arlacel 60 ® | 2% by weight (1) |
| Cetyl alcohol | 2% by weight |
| n-Propylparabene | 0.03% by weight |
| Phase B | |
| Glycerol | 5% by weight |
| Propylene glycol | 3% by weight |
| Tween 60 ® | 3% by weight (1) |
| Hamamelis extract | 1% by weight |
| Aloe Vera extract | 0.5% by weight |
| Croderm MF | 1% by weight (2) |
| Glydant ® | 0.3% by weight (3) |
| Methylparabene | 0.17% by weight |
| Water | 57% by weight |
| Phase C | |
| Perfume | QS |

(1) ICI-Atlas
(2) Croda
(3) Glyco

EXAMPLE XXVI

Night cream

| Phase A | |
|---|---|
| Avocado oil | 5% by weight |
| Wheat germ oil | 5% by weight |
| Jojoba oil | 5% by weight |
| Peanut oil | 5% by weight |
| Cetyl alcohol | 2% by weight |
| GMBW-2 | 5% by weight |
| Arlacel 60 ® | 2% by weight |
| Propylparabene | 0.03% by weight |
| Phase B | |
| Glycerol | 5% by weight |
| Propylene glycol | 3% by weight |
| Tween 60 ® | 3% by weight (1) |
| Algae extract | 1% by weight |
| Arnica extract | 1% by weight |
| Crolastin ® | 0.5% by weight (2) |
| Hydrosoy 2000 ® | 0.5% by weight (2) |
| Croderm MF | 1% by weight |
| Glydant ® | 0.3% by weight |
| Methylparabene | 0.17% by weight |
| Water | 55.6% by weight |
| Phase C | |
| Perfume | QS |

(1) ICI-Atlas
(2) Croda

EXAMPLE XXVII

Skin repair cream

| Phase A | |
|---|---|
| Paraffin oil | 20% by weight |
| Myglyol 8-12 ® | 10% by weight |
| Isopropyl meristate | 3% by weight |
| Modified beeswax | 5% by weight |
| Lanolin | 3% by weight |
| Cacao butter | 4% by weight |
| Avocado oil | 10% by weight |
| Arlacel 83 ® | 3% by weight |
| n-Propylparabene | 0.03% by weight |
| Phase B | |
| Glycerol | 4% by weight |
| Propylene glycol | 3% by weight |
| Crolastin ® | 0.5% by weight |
| Croderm ® | 0.5% by weight |
| Methylparabene | 0.17% by weight |
| Glydant ® | 0.3% by weight |
| Water | 33.5% by weight |
| Phase C | |
| Perfume | QS |

EXAMPLE XXVIII

A pigmented emulsion was prepared in a manner described in Example XXI using the following phases:

| Phase A | |
|---|---|
| C.I. 15585:1 | 5% |
| GMBW-2 | 12% |
| Silicone oil | 15% |
| Paraffin oil | 10% |
| Arlacel 60 ® | 3% |
| Phase B | |
| Tween 60 ® | 3% |
| Water | 52% |

A stable emulsion was obtained which showed no demixing phenomena over a period of 48 hours at 40° C.

The dispersions can be used for processing in:
flowable powders, lipsticks, mascaras;
pigmented creams, coloured pastes, mascaras and peel-off products.

EXAMPLE XXIX

The formation of microcapsules in an emulsion which contains modified beeswax.

An emulsion was made, made up of:

| Phase A | |
|---|---|
| modified beeswax (GMBW-2) | 8% by weight |
| hydrogenated lecithin | 3% by weight |
| cholesterol | 1% by weight |
| acetylated lanolin | 1% by weight |
| Phase B | |
| C.I. Acid Red 27 (Amaranth) | 0.3% by weight |
| 2,3-Butanedione | 0.7% by weight |
| Water | 86.0% by weight |

Phase A is heated to 65° C.; phase B is warmed rapidly to 65° C. to avoid excess evaporation of 2,3- butanedione, and with the exclusion of light to prevent premature oxidation of the pigment.

Phase A is then added to phase B and the mixture is homogenized and emulsified with a turbo mixer (3000 rpm) for 30 seconds. After the emulsion has formed it is stirred for 30 minutes with a paddle stirrer (30 rpm). The emulsion was then given the time for 24 hours to assume its final consistency. The emulsion thus obtained had an intense red colour and had a relatively low viscosity (* 150 cP; 25° C.).

The emulsion was then irradiated with light at 254 nm ($I=6.1 * 10^{-6}$ E/min), with stirring. The red colour had disappeared in about 3–4 minutes and the emulsion obtained had a blue glow. The emulsion was then broken by adding ethanol and warming to 110° C. The original red colour returned, although the optical density was considerably lower.

This phenomenon can only be explained by assuming that: I the oxidation of the pigment has taken place reversibly; or II microcapsules have formed, the content of which likewise contained the pigment solution.

The conclusion is that item II applies because with a shorter irradiation period the optical density of the broken emulsion does not change and item I cannot apply.

Comparison examples I–III

Examples XXVI to XXVII inclusive were repeated using normal beeswax. In each case a product which was not stable to heat and which showed phase separation was obtained. The emulsion obtained is, moreover, less pleasant on the skin and does not spread well. The skin feels greasy and sticky after use.

The cream with normal beeswax are in fact unsuitable for use.

I claim:

1. Process for the modification of beeswax, wherein the beeswax is allowed to react with glycidal in the ratio of 2.4 mol of glycidal per mol of beeswax at a temperature of 80° to 150° C. in the presence of 0.000.5 to 3% by weight of a basic catalyst, the phases are allowed to separate and the wax is recovered from the wax - containing phase.

2. Process according to claim 1, wherein 0.05 to 0.5% by weight base is used.

3. Process according to claim 1, wherein potassium carbonate is used as the base.

4. Process according to claim 1, wherein 15–40

5. Process for the modification of beeswax, wherein the beeswax is allowed to react with glycidol in the ratio of 2.4–4 mol of glycidol per mol of beeswax at a temperature of 80° C. to 150° C. in the presence of 0.0005 to 3% by weight of a basic catalyst, the phases are allowed to separate and the wax is recovered from the wax-containing phase.

6. Modified beeswax according to claim 5, having an acid number smaller than 5.

7. Modified beeswax according to claim 6, having an acid number smaller than 1.

8. Modified beeswax according to claim 7, wherein said modified beeswax has an acid number of not more than 0.1.

9. Emulsions, gels and dispersions obtained using modified beeswax according to claim 5.

10. Nanocapsules obtained using modified beeswax according to claim 5.

* * * * *

UNITED STATES PATENT AND TRADEMARK OFFICE
CERTIFICATE OF CORRECTION

PATENT NO. : 4,948,584
DATED : August 14, 1990
INVENTOR(S) : Hans M. Brand

It is certified that error appears in the above-identified patent and that said Letters Patent is hereby corrected as shown below:

Column 10 Line 25 "X" should read --x--.

Column 14 Line 29 after "593" insert --had--.

Column 18 Line 1 "cream" should read --creams--.

Claim 4 Line 15 Column 18 after "15-40" insert --mmol glycidol per kg beeswax per hour is added.--.

Delete present Claim 1 and insert the following:
 -- 1. Process for the modification of beeswax, wherein the beeswax is allowed to react with glycidol in the ratio of 2.4-4 mol of glycidol per mol of beeswax at a temperature of 80 to 150°C in the presence of 0.0005 to 3% by weight of a basic catalyst, the phases are allowed to separate and the wax is recovered from the wax-containing phase. --

Delete present Claim 5 and insert the following:
 -- 5. Beeswax modified by esterification of virtually all free acid therein, wherein the esterified free acid is attributable to the reactant glycidol. --

Signed and Sealed this

Nineteenth Day of January, 1993

Attest:

DOUGLAS B. COMER

Attesting Officer

Acting Commissioner of Patents and Trademarks